(12) United States Patent
Coffy et al.

(10) Patent No.: US 7,468,339 B2
(45) Date of Patent: Dec. 23, 2008

(54) DIKETONATE COMPLEX-DERIVED CATALYSTS USEFUL FOR PREPARING POLYOLEFINS

(75) Inventors: Tim J. Coffy, Houston, TX (US); Steven D. Gray, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 402 days.

(21) Appl. No.: 11/016,103

(22) Filed: Dec. 17, 2004

(65) Prior Publication Data

US 2006/0135350 A1 Jun. 22, 2006

(51) Int. Cl.
C08F 4/642 (2006.01)
B01J 31/02 (2006.01)

(52) U.S. Cl. .............. 502/115; 502/103; 502/104; 502/169; 526/124.2

(58) Field of Classification Search .......... 502/104, 502/103, 115, 171, 169; 526/124.2, 114, 526/124.3, 124.5, 348
See application file for complete search history.

(56) References Cited

U.S. PATENT DOCUMENTS

| | | | | |
|---|---|---|---|---|
| 4,107,413 A | 8/1978 | Giannini et al. | ............. | 526/114 |
| 4,114,319 A | 9/1978 | Governale | ............... | 49/488 |
| 4,220,554 A | 9/1980 | Scata et al. | ............. | 252/429 B |
| 4,294,721 A | 10/1981 | Cecchin et al. | ......... | 252/429 B |
| 4,439,540 A | 3/1984 | Cecchin et al. | ............. | 502/125 |
| 4,460,701 A | 7/1984 | Terano et al. | ............... | 502/104 |
| 4,562,173 A | 12/1985 | Terano et al. | ............... | 502/127 |
| 5,066,738 A | 11/1991 | Ewen | ............... | 526/124 |
| 6,693,058 B1 | 2/2004 | Gray et al. | ............... | 502/103 |
| 6,790,804 B2 * | 9/2004 | Gray et al. | ............... | 502/103 |
| 2005/0255990 A1 * | 11/2005 | Luinstra | ............... | 502/150 |

* cited by examiner

*Primary Examiner*—Caixia Lu
(74) *Attorney, Agent, or Firm*—Tenley R. Krueger

(57) ABSTRACT

An olefin polymerization catalyst may be prepared using a process including contacting a metal compound of the formula $M(OR_1)_2$ with a diketone to form a catalyst precursor having the general formula:

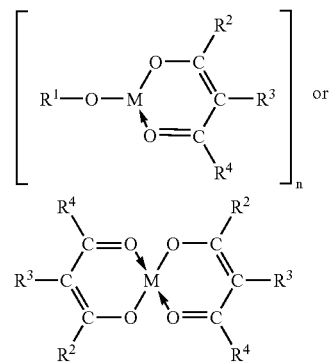

wherein M is a Group IIA metal; O is oxygen; n=1 or 2; $R_1$, $R_2$, $R_3$, and $R_4$ are the same or different; and are a hydrogen or a substituted or unsubstituted alkyl or aryl moiety having from about 1 to about 20 carbons atoms.

12 Claims, 1 Drawing Sheet

DIKETONATE COMPLEX-DERIVED CATALYSTS USEFUL FOR PREPARING POLYOLEFINS

BACKGROUND OF THE INVENTION

1. Technical Field

The invention relates to polyolefin catalysts, methods of making catalysts, and polymerization processes.

2. Background of the Art

Olefins, also called alkenes, are unsaturated hydrocarbons whose molecules contain one or more pairs of carbon atoms linked together by a double bond. When subjected to a polymerization process, olefins are converted to polyolefins, such as polyethylene and polypropylene. Ziegler-type polyolefin catalysts, their general methods of making, and subsequent use, are known in the polymerization art. While much is known about Ziegler-type catalysts, there is a constant search for improvements in their polymer yield, catalyst life, catalyst activity, amenability to use in large scale production processes, and in their ability to produce polyolefins having certain properties.

Conventional Ziegler-Natta catalysts comprise a transition metal compound generally represented by the formula:

$$MR^+_x$$

where M is a transition metal, $R^+$ is a halogen or a hydrocarboxyl, and x is the valence of the transition metal. Typically, M is a group IVB metal such as titanium, chromium, or vanadium, and $R^+$ is chlorine, bromine, or an alkoxy group. The transition metal compound is typically supported on an inert solid, e.g., magnesium chloride.

The properties of the polymerization catalyst may affect the properties of the polymer formed using the catalyst. For example, polymer morphology typically depends upon catalyst morphology. Acceptable polymer morphology differs for each class of production process (e.g., slurry loop, bimodal, gas phase, etc.), but typically includes uniformity of particle size and shape and an acceptable bulk density. Furthermore, there is a need in the art of preparing polymers to minimize the number of very small polymer particles (i.e., fines) to avoid plugging polymer transfer lines or solvent recovery systems.

SUMMARY OF THE INVENTION

In one aspect, the invention is a process for making a catalyst precursor, the process including contacting a metal compound of the formula $M(OR^1)_2$ with a diketone to form a bis(diketonate) having the general formula:

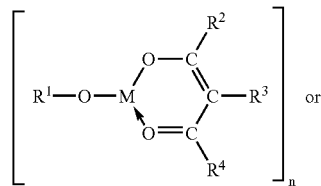

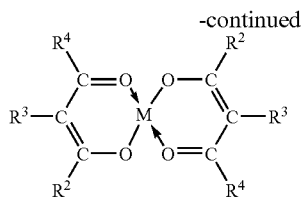

wherein M is a Group IIA metal; O is oxygen; n=1 or 2; $R^1$, $R^2$, $R^3$, and $R^4$ are the same or different; $R^1$, $R^2$, $R^3$, and $R^4$ are a substituted or unsubstituted alkyl or aryl moiety having from about 1 to about 20 carbons atoms or hydrogen.

In another aspect, the invention is a process for olefin polymerization, the process including contacting one or more olefin monomers together in the presence of a catalyst under polymerization conditions, wherein the catalyst is produced by a process including contacting a metal compound of the formula $M(OR^1)_2$ with a diketone to form a bis(diketonate) having the general formula:

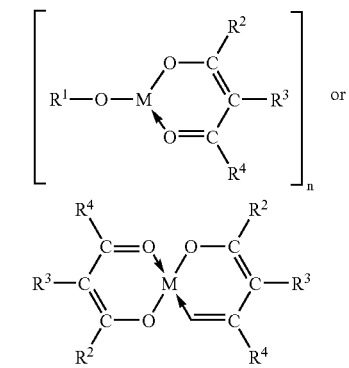

wherein M is a Group IIA metal; O is oxygen; n=1 or 2; $R^1$, $R^2$, $R^3$, and $R^4$ are the same or different; $R^1$, $R^2$, $R^3$, and $R^4$ are a substituted or unsubstituted alkyl or aryl moiety having from about 1 to about 20 carbons atoms or hydrogen.

Another aspect of the invention is a catalyst produced by a process including contacting a metal compound of the formula $M(OR^1)_2$ with a diketone to form a bis(diketonate) having the general formula:

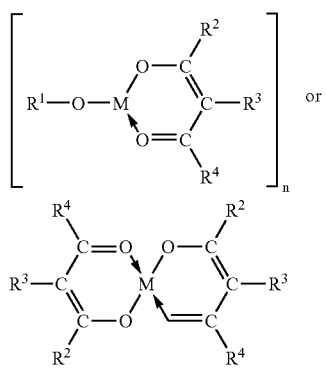

wherein M is a Group IIA metal; O is oxygen; n=1 or 2; $R^1$, $R^2$, $R^3$, and $R^4$ are the same or different; $R^1$, $R^2$, $R^3$, and $R^4$ are a substituted or unsubstituted alkyl or aryl moiety having from about 1 to about 20 carbons atoms or hydrogen.

An aspect of the invention is a polymer produced by a process including contacting one or more olefin monomers in the presence of a catalyst, the catalyst being produced by a process including contacting a metal compound of the formula $M(OR^1)_2$ with a diketone to form a bis(diketonate) having the general formula:

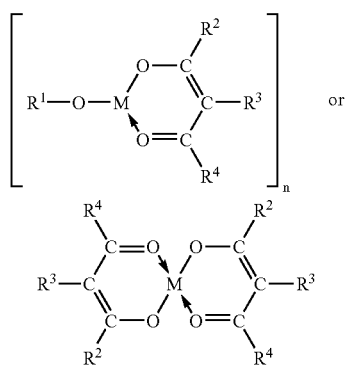

wherein M is a Group IIA metal; O is oxygen; n=1 or 2; $R^1$, $R^2$, $R^3$, and $R^4$ are the same or different; $R^1$, $R^2$, $R^3$, and $R^4$ are a substituted or unsubstituted alkyl or aryl moiety having from about 1 to about 20 carbons atoms or hydrogen.

In still another aspect, the invention is an article of manufacture including an article prepared using a polymer produced by a process including contacting one or more olefin monomers together in the presence of a catalyst under polymerization conditions, the catalyst having been produced by a process including contacting a metal compound of the formula $M(OR^1)_2$ with a diketone to form a bis(diketone) having the general formula:

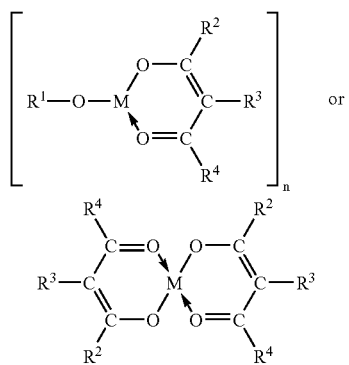

wherein M is a Group IIA metal; O is oxygen; n=1 or 2; $R^1$, $R^2$, $R^3$, and $R^4$ are the same or different; $R^1$, $R^2$, $R^3$, and $R^4$ are a substituted or unsubstituted alkyl or aryl moiety having from about 1 to about 20 carbons atoms or hydrogen.

The polymer may be formed into a film and employed in food packaging; the polymer may be formed by blow molding and the blown molded article may be a milk bottle, bleach bottle or a toy part; or the polymer may be formed into pipe and the article is a PE 100 pressure-rated pipe.

BRIEF DESCRIPTION OF THE DRAWING

For a detailed understanding and better appreciation of the invention, reference should be made to the following detailed description of the invention taken in conjunction with the accompanying drawings, wherein.

DETAILED DESCRIPTION OF THE INVENTION

Figure 1:
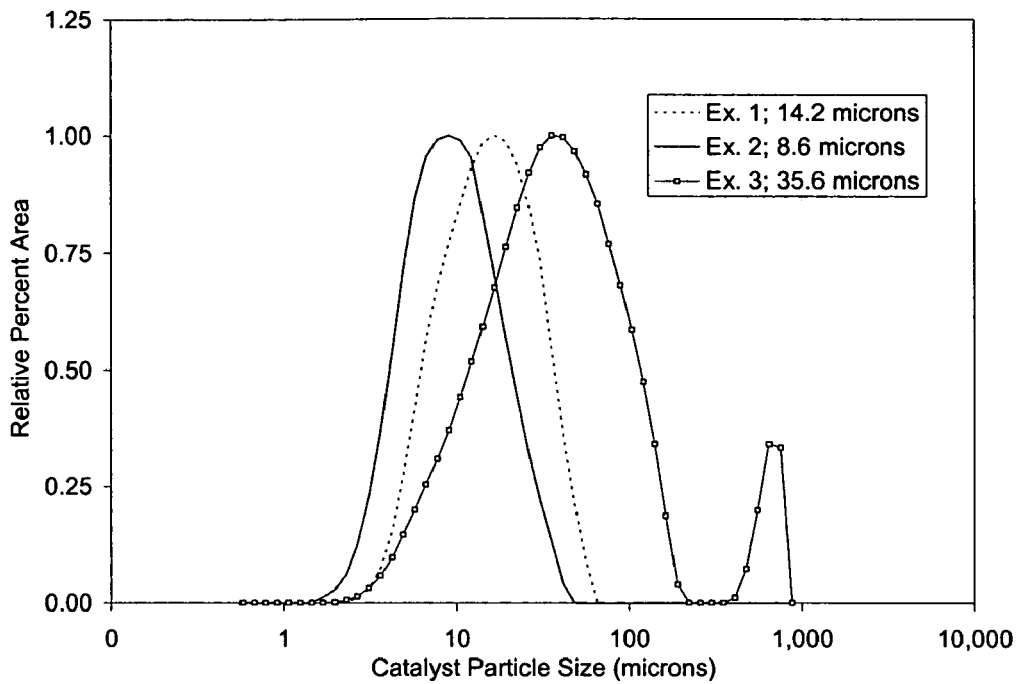
FIG. 1 is a graph showing the relative percent areas plotted against particle sizes in microns for the catalysts prepared in Examples 1, 2 and 3.

One commonly used polymerization process involves contacting an olefin monomer with a catalyst system that includes a conventional Ziegler-Natta catalyst, a co-catalyst, and one or more electron donors. Examples of such catalyst systems are provided in U.S. Pat. Nos. 4,107,413; 4,294,721; 4,439,540; 4,114,319; 4,220,554; 4,460,701; 4,562,173; and 5,066,738, which are incorporated herein by reference.

In an embodiment of the method of the invention, a catalyst precursor is obtained by the halogenation of a metal bis(diketonate). This metal bis(diketonate) itself may be formed by contacting a metal alkoxide with a diketone to form a bis (diketonate). The general formula of the metal alkoxide is $M(OR^1)_2$, wherein M is a group IIA metal, O is oxygen, and R is independently selected from among alkyl and aryl moieties. The general formula for the diketone is:

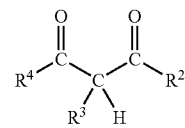

wherein $R^2$, $R^3$, $R^4$, are the same or different and $R^2$, $R^3$, and $R^4$, are hydrogen or a substituted or unsubstituted alkyl or aryl moiety. Alkyl or aryl moieties that may be used have from 1 to 20 carbons and include, but are not limited to, substituted alkyl radicals such as $-CF_3$, $-CCl_3$, and the like; radicals including Si and silicon ethers such as $-O-SiO_2$; and aryl radicals such as a nitrobenzyl radical and an anisole radical.

Suitable metal alkoxides may generally be described as having two alkoxide groups. The alkoxide groups may each be independently selected from among unsubstituted and substituted alkoxides having alkyl groups in the range of 1 to 10 carbons atoms. In one embodiment, the alkoxide groups have 1 to 4 carbon atoms, such as 2 to about 4 carbons atoms. Non-limiting examples of metal alkoxides suitable for use include magnesium alkoxides such as, for example, magnesium ethoxide.

In the practice of forming the metal bis(diketonate) of the invention, the metal alkoxide is generally contacted with the diketone under conditions suitable to yield the desired metal bis(diketonate) complex. Suitable temperatures for the contacting of the metal alkoxide with the diketonate are generally in the range of about –20° C. to about 100° C., desirably in the range of about 0° C. to about 50° C., and may be in the range of about 0° C. to about 25° C. The slurry may be heated to facilitate displacement substitution of the $OR^1$ group with the diketonate. In the practice of the invention, the metal alkoxide and diketone may be contacted together in any suitable solvent or reaction medium. Non-limiting examples of suitable solvents or reaction media include toluene, heptane, hexane, octane and the like.

Suitable diketonates include those of the general formula:

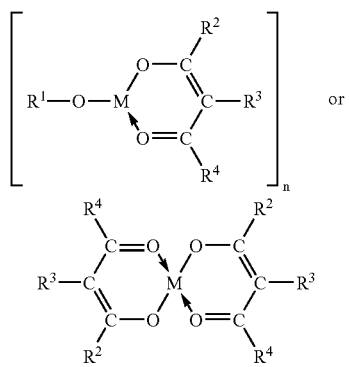

wherein n=1 or 2, and wherein $R^1$ is a substituted or unsubstituted alkyl or aryl group generally having from about 1 to about 20 carbons atoms, and wherein $R^2$, $R^3$, $R^4$ are as already defined. In the first or left of the two general formulas, the precursor can self dimerized by coordinating another oxygen to the metal substituent. In one embodiment, $R_1$, $R_2$, $R_3$, and $R_4$ have in the range of about 1 to about 8 carbons atoms, and may be in the range of about 1 to about 4 carbon atoms or hydrogen. A non-limiting example of suitable diketonates include those of the general formula wherein $R^1$ is an ethyl group, $R^2$ and $R^4$ are t-butyl groups and $R^3$ is hydrogen, and wherein n=1 or 2. A non-limiting example of a diketone suitable for use in the invention includes. 2,2,6,6,-tetramethylheptane-3,5-dione.

The electronic and steric properties of the diketone used in the reaction, as well as the amount employed, may greatly affect the final catalyst properties and performance. For example, using sterically encumbered ketones where any of $R^2$, $R^3$, and $R^4$ are large may provide a monomeric, three- or four-coordinate, soluble magnesium materials. The alkyl groups of the diketone may also be affect the electronic nature and overall solution behavior of the matters. For example, electron donating groups may be employed which electronically saturate the metal center and preclude the formation of dimeric or oligomeric species. Such materials are acceptable precursors for conversion to Ziegler-Natta catalysts with controlled morphologies.

The catalyst precursor may be further modified by contacting the bis(diketonate) with an organometallic agent. Suitable organometallic agents include but are not limited to aluminum alkyls, aluminum alkyl hydrides, lithium aluminum alkyls, zinc alkyls, magnesium alkyls and the like. Contacting the bis(diketonate) with the organometallic agents may reduce solution viscosity and may also reduce byproducts such as alcohols.

The catalyst precursor may be halogenated to form a catalyst support. It may also be titanated or titanated and halogenated to form a supported catalyst. Agents useful for halogenating the metal bis(diketonate) include any halogenating agent which, when utilized in the invention, will yield a suitable catalyst. Some of the halogenating agents may also serve as titanating agents useful for incorporating titanium into the catalyst precursor which is necessary to impart catalytic properties to the catalysts precursor. For example, $TiCl_4$ may both titanate and halogenate a catalyst precursor.

Metal chlorides may be desirable halogenating agents and/or titanating/halogenating agents. Non-limiting examples of suitable halogenating and/or titanating/halogenating agents include Group II, Group IV and Group V halides, hydrogen halides, or the halogens themselves. Specific examples of halogenating and/or titanating/halogenating agents are $BCl_3$, $AlCl_3$, $CCl_4$, $SiCl_4$, $TiCl_4$, $ZrCl_4$, $VOCl_4$, $VOCl_2$, $CrOCl_2$, $SbCl_5$, $POCl_2$, $PCl_5$, $HfCl_4$, and $Ti(OR)_nCl_{4-n}$, wherein R is an alkyl having 1 to 8 carbon atoms, and n is from 0 to 4. Mixtures of any of two or more of the foregoing may also be used as halogenating and/or titanating/halogenating agents. Other halogenating and/or titanating/halogenating agents include alkyl halo silanes of the formula $R'_nSiX_{(4-n)}$, wherein X is a halogen, R' is a substituted or unsubstituted hydrocarbyl having 1 to 20 carbon atoms, and n is 1-3

Possible halogenating and/or titanating/halogenating agents are $SiCl_4$, $TiCl_4$, $TiCl_n(OR)_{4-n}$, and mixtures of any of two or more of the foregoing. One embodiment employs as the halogenating agent a mixture of $TiCl_4$, and $Ti(OR)_4$, wherein R is a butyl group. The molar ratio of $TiCl_4$ to $Ti(OR)_n$ is generally in the range of about 4 to about 0.1, may be in the range of about 3 to about 1, and may be in the narrower range of about 2 to about 1.

In the practice of the invention, there is generally at least one halogenation step, and there may be two or more. A non-limiting example of a suitable halogenation treatment includes a first halogenation treatment with a mixture of $TiCl_4$ and $Ti(OR)_4$, followed by a second halogenation treatment with $TiCl_4$. Halogenation and titanation of catalysts and catalyst precursors is disclosed in U.S. Pat. No. 6,693,058 to Coffy, et al., the contents of which are incorporated herein by reference.

The halogenation and titanation of the metal bis(diketonate) may be carried out under conditions suitable to yield the desired catalyst component. Suitable temperatures for halogenating and titanating are generally in the range of about −20° C. to about 100° C., may be in the range of about 0° C. to about 75° C. and may be in the narrower range of about 25° C. to about 65° C.

In the practice of the invention, halogenation may be conducted at a molar ratio of halogenating agent to metal bis(diketonate) generally in the range of about 1 to about 20, may be in the range of about 1 to about 10, and may be in the narrower range of about 1 to about 8.

In the practice of the invention, the halogenating agent and the metal bis(diketonate) may be contacted together in any suitable solvent or reaction medium. Non-limiting examples of suitable solvents or reaction media include toluene, heptane, hexane, octane and the like.

In contrast to conventional practice, in an embodiment of the invention, a solid product precipitated in the halogenation and/or titanation step is the desired catalyst or support component that is then recovered by any suitable recovery technique. This desired catalyst or support component may then be utilized as a catalyst for the production of a controlled morphology Ziegler-Natta-type catalyst. The catalyst can be formed by direct precipitation of the three- or four-coordinate soluble intermediate, or it can be precipitated in the presence of a support template to form a supported catalyst. Silica or magnesium chloride can be used as a support template.

An internal electron donor for treating the catalyst or catalyst precursor may be used. The internal electron donor may be added during or after the halogenation step. Internal electron donors for use in the preparation of polyolefin catalysts are known, and any suitable internal electron donor may be utilized in the invention that will provide a suitable catalyst. Internal electron donors, also known as Lewis bases, are organic compounds of oxygen, nitrogen, phosphorous, or sulfur which are capable of donating an electron pair to the catalyst. The internal electron donor may be a monofunctional or polyfunctional compound, and may be selected from among the aliphatic or aromatic carboxylic acids and their alkyl esters, the aliphatic or cyclic ethers, ketones, vinyl esters, acryl derivatives, particularly alkyl acrylates or methacrylates and silanes. The amount of internal electron donor utilized may vary over a broad range and is generally in the range of about 0.01 to about 2 equivalents, but may be in the range of about 0.05 to about 0.5 equivalents. The catalyst precursor may be contacted with the internal electron donor for a contacting period in the range of about 0.5 hours to about 4 hours. In one embodiment a range of about 1 hour to about 2 hours is employed.

The catalyst made by the above described process may be combined with an organo-aluminum cocatalyst component to generate a catalyst system suitable for the polymerization of olefins. Typically, the cocatalysts which are used together with the transition metal containing catalyst are organometallic compounds of Group Ia, IIa, and IIIa metals such as aluminum alkyls, zinc alkyls, magnesium alkyls and the like. Organometallic compounds that may be employed in the practice of the invention are trialkylaluminum compounds.

External electron donors that may be added at the end of the preparation or utilized with the use of catalyst during polymerization and include those known in the art, including, but not limited to alkoxysilanes.

The catalysts described herein may be used for the polymerization of olefins, including α-olefins. For example, the present catalyst is useful for catalyzing ethylene, propylene, butylene, pentene, hexene, 4-methylpentene and other alkenes having at least 2 carbon atoms, and also for mixtures thereof. These catalysts may be utilized for the polymerization of ethylene to produce polyethylene, such as polyethylene with controlled powder morphology. Olefin polymerization methods are well known in general, and any suitable method may be utilized. The catalysts of the invention may offer improvements in one or more of the following properties: activity, morphology control, fines reduction, and hydrogen response.

In one embodiment, the polymers of the invention are converted into a film and the film used in food packaging. In another embodiment, the polymer is converted by blow molding and the molded article is a milk bottle, bleach bottle or toy part. In still another embodiment, the polymer is formed into pipe and the pipe is a PE-100 pressure-rated pipe.

The following non-limiting example is provided merely to illustrate the invention, and is not meant to limit the scope of the claims.

EXAMPLES

General Overview

A magnesium diketonate is prepared by treating $Mg(OEt)_2$ with diketones such as 2,2,6,6-tetramethylheptane-3,5-dione "TMDH-H" and pentane-2,4-dione "acac-H" and the resultant magnesium precursor is subjected to a variety of chlorination procedures to produce the final catalysts. All manipulations are performed under an inert atmosphere of argon or nitrogen using standard Schlenk-line and drybox techniques. Catalyst particle size data is obtained on the Malvern Mastersizer™ using catalyst slurry samples taken at various stages of the catalyst preparation. Fluff particle size data is obtained by sieving analyses using a CSC Scientific Sieve Shaker™. Polymerization reactions are performed under the following standard conditions: Temperature of 80° C.; pressure of 125 psi; $H_2:C_2$ molar ratio of 0.25; reaction time of 60 minutes; TEAI cocatalyst at 0.25 mmol/L relative to diluent; polymerization solvent 2.0 liters hexane.

Raw Materials $Mg(OEt)_2$ is obtained from Hüls and heated at 120° C. under dynamic vacuum for 12 hours prior to use to remove residual alcohol. Tetraethyl aluminum "TEAI," 24.8% by weight in heptane, is purchased from Akzo and used as received. TMHD-H, ACAC-H, $TiCl_4$, and, $Ti(OBu)_4$ "TBNT" are purchased from Aldrich and used as received. Heptane and hexane are purified by passing them through a column of 3A molecular sieves, a F200 alumina column, and a column of BASF R3-11 copper catalyst at a rate of 12 mL/min prior to use.

Example 1

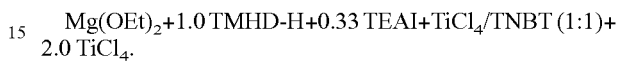

In a drybox, a five-necked, one-liter flask is equipped with a 125 mL addition funnel, a mechanical stirring shaft with a flat-bottomed, half moon-shaped paddle, a condenser with a gas inlet, a thermometer, and a septum. The flask is charged with $Mg(OEt)_2$ (2.5 g, 22 mmol) and brought to the Schlenk line where it is placed under a rapid argon purge. Heptane (100 mL) is added to the flask and the mixture is agitated at 150 rpm.

A solution of TMHD-H (4.05 g, 22 mmol), diluted to 100 mL total volume with heptane, is added dropwise to the $Mg(OEt)_2$ slurry over the course of 35 minutes. The solution becomes cloudy with the TMDH-H addition. Gradually, the solution begins to clear as the $Mg(OEt)_2$ is reacted. The pale yellow, solids-containing mixture is next heated to reflux. The solution gradually clears with heating. Upon reaching about 80° C., a component of the solution is seen to reflux. Heating is continued until the solution temperature reaches 95° C. and the mixture is then allowed to react at this temperature for 1 hour.

The reaction is then allowed to cool to 55° C. and a solution of TEAI (0.83 g, 7.3 mmol), diluted to 50 mL total volume in heptane, is slowly added. The yellow color of the solution initially intensifies, then fades throughout the course of the 25 minute TEAI addition. The solution is allowed to stir at 55° C. for 30 minutes.

To the reaction is next added dropwise a mixture of $Ti(OBu)_4$ (7.5 g, 22 mmol) and $TiCl_4$ (4.5 g, 24 mmol) in 120 mL heptane. Immediate reaction is seen as the $Ti(OBu)_4$/TiCl4 mixture contacts the solution. At the solution interface, a bright yellow color is seen which rapidly dissipates as the components are mixed with the bulk solution. After 25 mL of the mixture has been added, the solution turns a slight green color. The solution becomes thick with solids and the color intensifies over the course of the 1 hour addition.

The mixture is next allowed to stir at 55° C. for 1 hour. The agitation is discontinued and the solids are allowed to settle. The forest green solution is removed via cannula and the resultant solid is washed with heptane (3×250 mL). The supernatant grows less colored with each washing. The final yellow solid is reslurried in heptane (250 mL) and allowed to stand overnight.

A solution of $TiCl_4$ (5.0 mL, 46 mmol) diluted to 50 mL total volume with heptane is next added dropwise to the slurry over the course of 2 hours. The slurry rapidly turns bright orange upon $TiCl_4$ addition. This color intensifies with time and the mixture is allowed to stir at 55° C. for 1.5 hour. The agitation is then discontinued and the solution is allowed to settle. The settling of the solid is rapid and uniform. The now orange solid is washed with heptane (3×25 mL). The final orange solid is re-suspended in heptane (250 mL) to yield the final catalyst slurry.

Example 2

Mg(OEt)$_2$+2.0 TMHD-H+0.67 TEAI+TiCl$_4$/TNBT (1:1)+ TiCl$_4$.

In a drybox, a five-necked, one-liter flask is equipped with a 125 mL addition funnel, a mechanical stirring shaft with a flattened, half moon-shaped paddle, a condenser with a gas inlet, a thermometer, and a septum. The flask is charged with Mg(OEt)$_2$ (2.5 g, 22 mmol) and brought to the Schlenk line where it is placed under a rapid argon purge. Heptane (100 mL) is added to the flask and the mixture is agitated at 150 rpm.

A solution of TMHD-H (8.11 g, 44 mmol) diluted to 100 mL total volume with heptane is added dropwise to the Mg(OEt)$_2$ slurry. Immediate reaction is seen as the solution becomes cloudy as the large Mg(OEt)$_2$ particles are seen to be broken down upon reaction. The solution is then heated to reflux. With heating, the solution becomes slightly yellow in color and the solids dissolve until only a small amount of fine, white material is observed in the solution. Upon reaching about 80° C., a component of the solution is seen to reflux. Heating is continued until the solution temperature reaches 95° C. and the mixture is then allowed to react for 1 hour.

The mixture is next cooled to 55° C. A solution of TEAI (1.67 g, 14.7 mmol), diluted to 50 mL total volume in heptane, is then added dropwise to the slurry. Gradually, the yellow color of the solution is seen to fade with the TEAI addition. Addition is complete in 10 minutes and the clear, mobile solution is allowed to stir at 55° C. for 30 minutes.

To the reaction is next added dropwise a mixture of Ti(OBu)$_4$ (7.5 g, 22 mmol) and TiCl$_4$ (4.5 g, 24 mmol) in diluted to 120 mL total volume with heptane. The immediate formation of a fine white precipitate is seen upon Ti(OBu)$_4$/TiCl$_4$ addition and the solution turns yellow. After 25 mL of the mixture has been added, the solution turns deep blue. The color intensifies over the course of the 2 hour addition. The mixture is then allowed to stir at 55° C. for 1 hour.

The solid is next washed with heptane (3×250 mL). The supernatant becomes less blue with each washing. The final white solid is reslurried in heptane (250 mL) and allowed to cool to room temperature.

A solution of TiCl$_4$ (4.4 g, 23 mmol) diluted to 100 mL total volume with heptane is next added dropwise to the slurry. The slurry rapidly turns orange upon TiCl$_4$ addition. The addition is complete in 85 minutes and the mixture is allowed to stir for 1 hour.

The agitation is discontinued and the solution is allowed to settle. The solution is slightly yellow and the solid is orange. The solid is washed with heptane (3×25 mL) and the final pale orange solid is reslurried with heptane (250 mL). This solid is the final catalyst.

Example 3

Mg(OEt)$_2$+1.0 ACAC-H+0.33 TEAI+1.0 TNBT+1.0 TiCl$_4$+2.0 TiCl$_4$

In a drybox, a five-necked, one-liter flask is equipped with a 125 mL addition funnel, a mechanical stirring shaft with a flattened, half moon-shaped paddle, a condenser with a gas inlet, a thermometer, and a septum. The flask is charged with Mg(OEt)$_2$ (2.5 g, 22 mmol) and brought to the Schlenk line where it is placed under a rapid argon purge. The solid is slurried with hexane (100 mL) and agitated at 150 rpm.

A solution of acac-H (2.2 g, 22 mmol), diluted with heptane to 100 mL total volume, is added dropwise to the slurry. The solution becomes cloudy throughout the acac-H addition, eventually forming a milky white slurry. The mixture is then heated to 95° C. With heating, the solution becomes mobile and at about 80° C., a component is seen to reflux. At 85° C., the solution becomes clearer as some of the white solid dissolves. The solution is allowed to stir for 1 hour at solvent reflux temperature.

The reaction mixture is allowed to cool to 60° C. and a solution of TEAI (3.4 g, 7.3 mmol) diluted to 50 mL total volume with heptane is added dropwise over the course of 40 minutes. The cloudy solution gradually begins to clear with time, with a small amount of solid persisting. The addition funnel employed to add the TEAI is rinsed with heptane (2×25 mL) and the reaction is allowed to proceed at 65° C. for 1 hour.

A solution of TNBT (7.5 g, 22 mmol), diluted to 50 mL total volume with heptane, is next added dropwise to the solution over the course of 45 minutes. The resultant clear, yellow solution is stirred for 1 hour and a solution of TiCl$_4$ (2.25 g, 12 mmol) diluted to 25 mL total volume with heptane is next added slowly to the mixture. Immediately upon contacting the solution, a bright yellow color is seen which rapidly dissipates as the reagents are mixed. Gradually, the solution turns a deep green color and the formation of a large amount of white solid is seen. The addition is complete in 80 minutes and the resultant deep forest green slurry is allowed to react for 1 hour. Over this time, more white solid is seen to form as the solution gradually turns a deep blue color. The temperature is then lowered to 50° C.

After 12 hours agitation is discontinued and the solids are allowed to settle. The solid settling occurs relatively uniformly, but also slowly. The deep blue supernatant is then decanted from the white solid. The solid is reslurried in heptane (250 mL) and allowed to stand at 40° C. overnight to extract any remaining byproducts (presumably highly-colored, titanium diketonate complexes). After 12 hours, the solid is washed with heptane (3×250 mL). The deep blue supernatant grows fainter with each wash. The resultant white solid is then reslurried in heptane (250 mL) and a solution of TiCl$_4$ (4.5 g, 24 mmol), diluted to 50 mL total volume with heptane, is added dropwise to the slurry. The slurry rapidly becomes orange throughout the 30 minute addition. The mixture now appears as a bright orange solution containing a pale orange solid.

After 1.5 hour agitation is discontinued and the solid is allowed to settle, which occurs rapidly. In addition to the solid, orange crystals are seen at this time. The solid is washed with heptane (3×250 mL) and reslurried to provide the final catalyst as a bright orange powder in heptane.

Examples 4-6

The catalysts prepared in Examples 1, 2 and 3 are examined for morphology and ability to perform as catalysts in standard ethylene polymerizations.

FIG. 1 is a graph showing the relative percent area for each powder plotted against the particle sizes, wherein particle size in microns is shown as a logarithmic scale. From this graph it can be seen that the catalysts prepared in Examples 1 and 2 have relatively narrow size distributions, with the catalyst of Example 1 having an average diameter of 14.2 microns and the catalyst of Example 2 having an average diameter of 8.6 microns. Neither of these powders showed significant amounts of particles of less than 5 microns. This is highly desirable, since so-called "catalyst fines", i.e., very small particles, can lead to problems when such catalysts are employed in large scale production processes. The catalyst prepared in Example 3 has a somewhat wider particle size distribution, but its average particle diameter of about 35.6 microns makes it, too, a desirable choice for large scale production processes. The examples demonstrate changes in the steric and electronic nature of the diketonate precursor complex influence catalyst morphology and performance.

Figure 2:
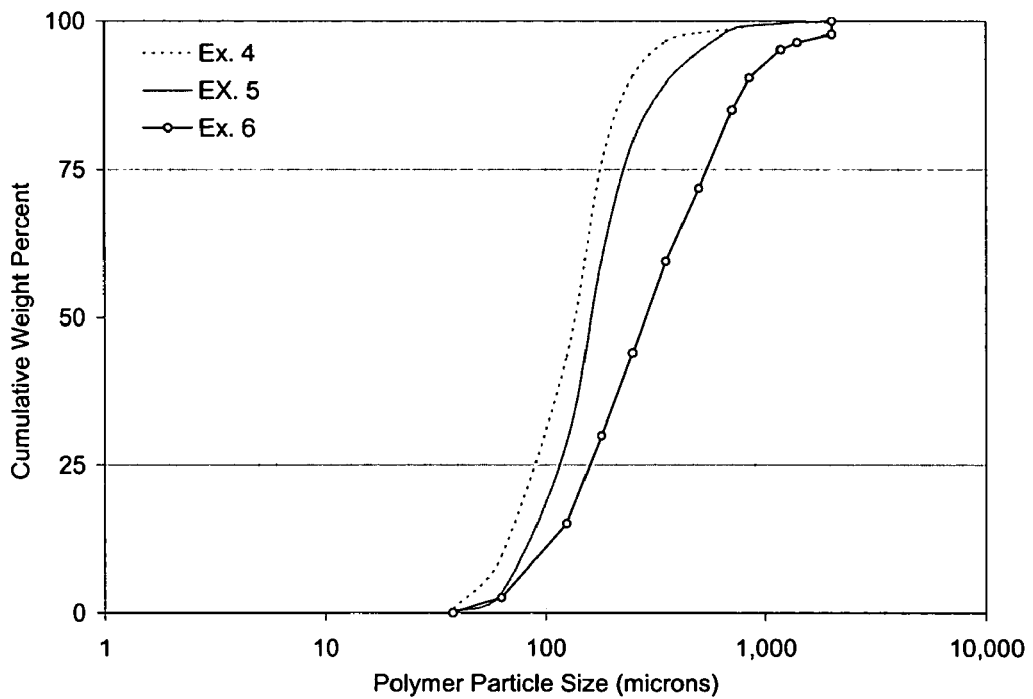
FIG. 2 is a graph showing the polymer particle size plotted against cumulative weight percent for polymers prepared in Examples 4, 5, and 6.

Polymer morphology data are presented in FIG. 2. The catalysts prepared in Examples 1, 2 and 3 are also each employed in a standard polymerization to prepare high density polyethylene (HDPE), in order to determine their overall polymerization effectiveness by examining their activity and the quality of the resins being produced. A comparative polymerization is also carried out under identical conditions but using catalyst prepared by direct interaction of relatively insoluble $Mg(OEt)_2$ suspensions with $TiCl_4$ at elevated temperatures, a conventional Ziegler-Natta preparation. It will be seen from the information in the Table hereinbelow that, under identical conditions, the catalysts of Examples 1 and 2 display higher activity, reported as conversions of greater than 30,000 g PE/g catalyst, than is seen in the comparative polymerization. The catalysts of Examples 1 and 2 also show a higher response of melt flow to hydrogen than the catalyst used in the comparative polymerization. This higher "hydrogen response" may help to improve catalyst life in production processes where maximum reactor pressure restrictions may limit ethylene saturation.

Bulk powder data is also obtained and recorded in the Table. As expected, the powder morphologies reflect the catalyst particle size data shown in FIG. 1. Using the catalysts of Examples 1 and 2 results in polymers having uniform particle size distributions with low fines levels. In particular, the Example catalysts result in afford extremely low levels of small polymer particles (those less than 38 microns) without a significant compromise of the overall powder bulk density. The catalyst from Example 3 yields a broad span of polymer particle sizes and a larger overall average particle size as expected from the catalyst distribution. As for the polymerizations using the catalysts of Examples 1 and 2, however, the polymerization using the catalyst of Example 3 also does not produce a significant number of undesirably small polymer particles. These observations illustrate an overall improvement of catalyst and polymer morphology obtained from the inventive catalysts.

While the illustrative embodiments of the invention have been described with particularity, it will be understood that various other modifications will be apparent to, and may be readily made by, those skilled in the art without departing from the scope of the invention. Accordingly, it is not intended that the scope of the claims appended hereto be limited to the examples and descriptions set forth herein but rather that the claims be construed as encompassing all the features of patentable novelty which reside in the invention, including all features which would be treated as equivalents thereof by those skilled the art to which this invention pertains.

What is claimed is:

1. A process for making a catalyst precursor, the process comprising contacting a metal compound of the formula $M(OR_1)_2$ with a diketone to form a bis(diketonate) having the general formula:

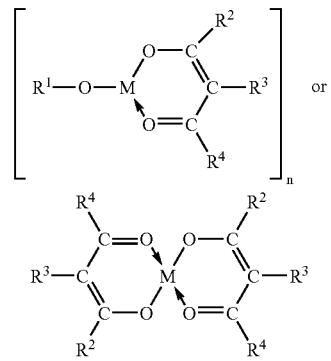

wherein M is a Group IIA metal; O is oxygen; n=1 or 2; $R^1$, $R^2$, $R^3$, and $R^4$ are the same or different; and are a hydrogen or a substituted or unsubstituted alkyl or aryl moiety having from about 1 to about 20 carbons atoms; and contacting the bis(diketonate) with an organometallic agent.

2. The process of claim 1 wherein M is magnesium and $R^1$ is an ethyl group.

TABLE

|  | Example Polymer | | | |
| --- | --- | --- | --- | --- |
|  | Comp. Ex. | Ex 4 | Ex. 5 | Ex. 6 |
|  | Catalyst Used | | | |
|  | Comp. Ex. | Ex. 1 | Ex. 2 | Ex. 3 |
| Catalyst Slurry Charge (mL) | n/a | 1.25 | 1.0 | 0.8 |
| Ethylene Flow Rate (SLPM) | 8.0 | 8.0 | 8.0 | 8.0 |
| Hydrogen Flow (SLPM) | 2.0 | 2.0 | 2.0 | 2.0 |
| Activity (g PE/g catalyst/h) | 27,000 | 34,700 | 32,100 | 4,800 |
| Powder Bulk Density (g/mL) | 0.30 | 0.29 | 0.28 | 0.12 |
| Average Polymer Size (μ) | 280 | 135 | 160 | 290 |
| Polymer Fines (wt %, 38μ) | 2.4 | 0.6 | 0.2 | 0.0 |
| Powder $MI_5$ (dg/min) | 0.66 | 1.62 | 1.59 | 0.21 |
| Powder HLMI (dg/min) | 7.5 | 18.6 | 18.3 | 2.0 |
| Powder $SR_5$ (HLMI/MI5) | 11.3 | 11.7 | 11.4 | 9.6 |
| Resin Density (g/mL) | 0.9560 | 0.9597 | 0.9554 | 0.9614 |

3. The process of claim 1 wherein the diketone is 2,2,6,6,-tetramethylheptane-3,5-dione or pentane-2,4-dione.

4. The process of claim 1 further comprising contacting the bis(diketonate) with a first halogenating and/or halogenating/titanating agent to form a halogenated catalyst precursor.

5. The process of claim 4 further comprising contacting the halogenated catalyst precursor with a second halogenating and/or halogenating/titanating agent.

6. The process of claim 1 further comprising contacting the bis(diketonate) with a titanating agent to form a catalyst precursor.

7. The process of claim 6 further comprising contacting the catalyst with a halogenating agent.

8. The process of claim 4 wherein the first halogenating and/or halogenating/titanating agent is a mixture of $Ti(OBu)_4$ and $TiCl_4$.

9. The process of claim 5 wherein the second halogenating and/or halogenating/titanating agent is $TiCl_4$.

10. The process of claim 1 wherein the organometallic agent comprises an organo-aluminum compound.

11. The process of claim 1 further comprising adding at least one internal electron donor.

12. The process of claim 1 further comprising precipitating the bis(diketonate) with a support material.

* * * * *